US005869059A

United States Patent [19]
Garza

[11] Patent Number: 5,869,059
[45] Date of Patent: Feb. 9, 1999

[54] HERBAL COMPOSITION FOR HEMORRHOID TREATMENT

[75] Inventor: Mercedes Flores Garza, Houston, Tex.

[73] Assignee: Mon's Tea Partnership, Houston, Tex.

[21] Appl. No.: 585,833

[22] Filed: Jan. 16, 1996

[51] Int. Cl.⁶ .................................................. A61K 35/78
[52] U.S. Cl. ........................ 424/195.1; 514/882; 514/886
[58] Field of Search ..................................... 514/882, 886; 424/195.11, 195.1

[56] References Cited

U.S. PATENT DOCUMENTS

| | | | |
|---|---|---|---|
| 272,138 | 2/1883 | Holder | 424/195.1 |
| 481,815 | 8/1892 | Page et al. | 424/195.1 |
| 1,383,896 | 5/1921 | Wood | 424/195.1 |
| 1,890,596 | 12/1932 | Zographos | 424/645 |
| 3,062,716 | 11/1962 | Montandraud | 514/56 |
| 3,464,972 | 9/1969 | Rocher | 536/18.5 |
| 3,534,102 | 10/1970 | Waldstein | 564/301 |
| 3,594,473 | 7/1971 | Hunger et al. | 514/25 |
| 3,781,424 | 12/1973 | Ponvert | 424/195.1 |
| 3,935,310 | 1/1976 | Homan | 424/195.1 |
| 4,118,480 | 10/1978 | Williams | 424/131 |
| 4,169,143 | 9/1979 | Haimowitz et al. | 424/195.1 |
| 4,192,866 | 5/1980 | Anderson | 424/697 |
| 4,202,825 | 5/1980 | Taya et al. | 260/345.2 |
| 4,265,887 | 5/1981 | Breskman | 424/201 |
| 4,383,986 | 5/1983 | Dubash et al. | 424/443 |
| 4,626,433 | 12/1986 | Gros | 424/154 |
| 4,761,285 | 8/1988 | Vasilion et al. | 424/195.1 |
| 4,945,084 | 7/1990 | Packman | 514/53 |
| 4,985,257 | 1/1991 | Verde | 424/705 |
| 5,002,767 | 3/1991 | Masse | 424/195.1 |
| 5,196,405 | 3/1993 | Packman | 514/53 |
| 5,234,914 | 8/1993 | Gallina | 514/54 |
| 5,266,571 | 11/1993 | Amer | 514/252 |
| 5,403,867 | 4/1995 | Okumura et al. | 514/573 |

OTHER PUBLICATIONS

A Useful Guide to Herbal Health Care, Health Center for Better Living,6189 Taylor Rd.,Naples,Fla. p.38 Home Herbal, Penelope Ody,Dorling Kindersley,London and New York 1995.
Natural Prescriptions, Robert M. Giller,M.D. ? 1994.
The Complete Medicinal Herbal, Penelope Ody, Dorling Kindersley,London and New York, 1993.
The Natural Pharmacy, Miriam Poulunin and Christopher Robbins, Collier Books/Macmillan,New York 1992.
The Visual Dictionary of Plants,edited by Bryan Walls and Mary Lindsay,Dorling Kindersley, New York 1992.
The Doctor's Book of Home Remedies, Prevention/Rodale Press, 1991.
The Complete Shopper's Guide to Natural Foods, Christopher Kilham, N.D. Autumn Press/Random House 1980.
The Complete Book of Natural Medicines, David Carroll, ?, 1980.
The Complete Book of Herbs and Spices, Claire Lowenfield and Phillippa Back, G.P.Putnam's Sons,NY, 1974.
Trees, Leaves, Bark and Fruit, Jaromir Pokorny,Octupus Books,London,1973.
Horsetail Grass Tea Bags, Alvita, A TwinLab Company since 1922.
The Complete Medicinal Herbal,Penelope Ody,pp.55,154, and 172.
Phytochemical Investigation of Amphipterygium adstringens,Edward E. Gonzalez and Jaime N. Delgado, vol. 51,No.8,Aug.1962.
Journal of Pharmaceutical Science—( pp. 786,787,788,789, 790).
Journal of Ethnopharmocology,34 (1991) 147–154,Elsevier Scientific Publishers (Ireland,Otd.).
Actacryst (1987) vol. C43, pp. 990–992.
Structure and Stereochemistry of the Methyl Ester of (5a, 13a,14b,17a,20S,24Z).
M. Sorbiano–Garcia,et al, Instituto de Quimica,Universidad Nacional Automoma de Mexico, Circuito Exterior,Ciudad Universitar Coyoacan 04510,Mexico DF).
Foster et al, 1990, a field Guid to Medicinal Plant1, Houghton Mifflin Co. ISBN 0–395–35309–2, p. 304.

*Primary Examiner*—Mary E. Mosher
*Assistant Examiner*—Ali R. Salimi
*Attorney, Agent, or Firm*—Lackenbach Siegel Marzullo Aronson & Greenspan, P.C.

[57] ABSTRACT

An anti-hemorrhoidal composition, tea, and kit containing tea bags including, in combination, a first herb of the genus Equisetaceae and a second herb of the Generic Juliania, family Julianiaceae, genus *Amphipterygium adstringens* (also known as "Cuachalalate.") is provided herein. Further provided herein is a method of treating hemorrhoids and a method for making an anti-hemorrhoidal composition.

24 Claims, 1 Drawing Sheet

HERBAL COMPOSITION FOR HEMORRHOID TREATMENT

This is invention relates to a treatment for hemorrhoids and symptoms thereof; and, more particularly, it relates to a composition of matter, tea, kit and treatment for the condition of hemorrhoids.

BACKGROUND OF THE INVENTION

Various diseases of the anorectal region of the human body are characterized by inflammation, itching, and ulcerations. The anorectal region is generally comprised of the anus, rectum, and lower colon. In particular, hemorrhoids or piles are a common ailment of the anorectal region, and may be internally or externally located in the anorectal area. Notwithstanding their location, veins in the anorectal area become inflamed and frequently result in itching. The causes of hemorrhoids include predisposing causes such as erect posture, heredity, occupation and diet, constipation, diarrhea, pregnancy, anal infection, pelvic tumors, rectal carcinoma, cardiac failure, portal hypertension, vomiting and physical exertion.

Many remedies are known for the alleviation of these symptoms. Most of the remedies in the art have varying degrees of success, and few remedies have been successful in substantially reducing or completely eliminating hemorrhoidal symptoms without undesirable side effects.

That is, there are undesirable side effects of these known treatments. It is these undesirable side effects of these treatments that frequently prevent users of these treatments from obtaining adequate relief. Hence, there exists a need for a treatment for hemorrhoids that substantially or completely eliminates hemorrhoids, while being free of undesirable side effects associated with the treatment.

The prior art has suggested the therapeutic utility of certain unknown compounds of various herbs. In particular, U.S. Pat. No. 481,815 to Page et al. describes a herbal composition comprised of *Acacia farnesiana, Acacia constricta*, and *Flourensia cornua*; U.S. Pat. No. 272,138 to Holder discloses an ointment comprising *Anthemis cotula*; U.S. Pat. No. 3,781,424 to Ponvert discloses a composition comprising extracts of *Capsicum annum*; U.S. Pat. No. 1,383,896 to Wood et al. discloses an ointment comprising extracts of Gnaphalium, Balm of Gilead buds, and elder bark; U.S. Pat. No. 1,890,596 to Zographos discloses an ointment comprising extracts of powdered calomel and green tansy weed; U.S. Pat. No. 3,935,310 to Homan discloses a composition comprising extracts of *Celastrus scandens*; U.S. Pat. No. 4,761,285 to Vasiliou et al. discloses a composition comprising extracts of Leptandra root, chick peas and grape seeds; U.S. Pat. No. 3,464,972 to Rocher discloses a composition comprising extracts of *Ficaria ranunculus*; and, U.S. Pat. No. 5,002,767 to Masse discloses a composition comprising extracts of the Resedaceae family. Yet none of these compositions involve the use of the combination of the herbs described in the present invention.

Further, the treatment of hemorrhoids is complicated by the fact that during defecation, the fecal mass stretches, tears and irritates the already inflamed and swollen hemorrhoidal tissue. Further, as a result of additional muscle strain during defecation resulting from the physical movement of the fecal mass through the already swollen and inflamed tissue, herniation of the anal walls frequently results. Moreover, the excretory tract is the site of numerous organisms that are infectious and that enjoy infiltrating the anal cavity herniations. This infiltration further damages already damaged tissue and aggravates the healing process. If left untreated hemorrhoids often worsen and require surgery to remove the diseased hemorrhoidal tissue.

Treatments of hemorrhoids have tended to focus on topical applications of creams and lotions and suppositories having medicaments therein that have sought to relieve itching (Pruritis ani) and/or inflammation. The efficacy of the prior art treatments in relieving or curing a variety of symptoms is uncertain. Exemplary such creams or lotions are described in: U.S. Pat. No. 4,169,143 to Haimowitz which discloses a treatment of hemorrhoids with compositions comprising Vitamin E; U.S. Pat. No. 3,062,716 to Montandraud which discloses a treatment of hemorrhoids with compositions comprising heparin; U.S. Pat. No. 3,534,102 to Waldstein which discloses a treatment of hemorrhoids with compositions comprising reaction products of elemental iodine and alkoxylated alkylamine oxides; U.S. Pat. No. 3,594,473 to Hunger et al. which discloses a treatment of hemorrhoids with compositions comprising reaction products of ethyl-3,5,6-tri-O-benzyl-D-glucofuranoside; U.S. Pat. No. 5,266,571 to Amer discloses a treatment of hemorrhoids with 5-hydroxytryptamine antagonist; U.S. Pat. No. 4,945,084 to Packman discloses a treatment of hemorrhoids with disaccharide polysulfate-aluminum compounds; U.S. Pat. No. 4,118,480 to Williams discloses a treatment of hemorrhoids with a mixture of compounds; U.S. Pat. No. 4,202,825 to Taya discloses a treatment of hemorrhoids with a derivative of quercetin; U.S. Pat. No. 4,265,887 to Breskman discloses a treatment of hemorrhoids with a mixture of vitamins; U.S. Pat. No. 4,626,433 to Gold discloses a treatment of hemorrhoids with a salve comprising aluminum potassium sulfate, linseed oil, methanol, camphor and pure petroleum jelly; U.S. Pat. No. 4,985,257 to Verde discloses a treatment of hemorrhoids with a composition comprising cream of tartar; U.S. Pat. No. 5,196,405 to Oakman discloses a treatment of hemorrhoids with a composition comprising disaccharide polysulfate-aluminum compounds; U.S. Pat. No. 5,234,914 to Gallina discloses a treatment of hemorrhoids with a composition comprising hyaluronic acid; and, U.S. Pat. No. 5,403,867 to Okumura discloses a treatment of hemorrhoids with a composition having antipruritic properties. However, all of the topical preparations have the drawback of further agitating already swollen and inflamed tissue by the manual application of the medicament. Further, there may be hemorrhoids located deep within the anal rectal cavity that are inaccessible from the exterior thereof for the topical application of medicaments. Hence, there exists a need for an edible composition that can be taken orally for the relief and treatment of internal hemorrhoids and hemorrhoidal symptoms. It is an object of the present invention to solve the problems in the art.

SUMMARY OF THE INVENTION.

It is a further object of the present invention to provide a low cost, effective cure for the treatment of hemorrhoids with no side effects. An anti-hemorrhoidal composition, tea, and kit containing tea bags including, in combination, a first herb of the genus Equisetaceae and a second herb of the family Julianiaceae, genus *Amphipterygium adstringens* is provided herein. The herb from the genus Equisetaceae is selected from the group consisting of Horsetail, *Equisetum arvense, Equisetum hyemale, Equisetum fluviatile, Equisetum kansanum, Equisetum litorale, Equisetum palustre, Equisetum pratense, Equisetum scirpoides, Equisetum sylvaticum, Equisetum Telemateia, Equisetum variegatum, Equisetum debile, Equisetum elongatum, Equisetum giganteum*, and *Equisetum maximum*. The herb from the genus *Equisetum arvense* is selected from the group consisting of *Equisetum arvense* var. boreale, *Equisetum arvense* forma alpestre, *Equisetum arvense* forma campestre, *Equisetum arvense* forma diffusum, *Equisetum arvense* forma pseudo-alpestre, *Equisetum arvense* forma pseudo-silvaticum, *Equisetum arvense* forma pseudo-varium, *Equisetum arvense* forma ramulosum, and *Equisetum arvense* forma varium.

Optionally, the herb, *Equisetum hyemale*, is selected from the group consisting of *Equisetum hyemale* var. affine, *Equisetum hyemale* var. intermedium, *Equisetum hyemale* var. rubustum, *Equisetum hyemale* forma polystachyum, *Equisetum hyemale* forma proliferum, and *Equisetum hyemale* forma pumilum, the herb, *Equisetum palustre*, is selected from the group consisting of *Equisetum palustre* forma arcuatum, *Equisetum palustre* forma filiforme, *Equisetum palustre* forma fluitans, *Equisetum palustre* forma nigridens, *Equisetum palustre* forma polystachion, *Equisetum palustre* forma ramulosum, *Equisetum palustre* forma verticilatum, and *Equisetum palustre* forma simplex, and the herb, *Equisetum Telemateia*, is selected from the group consisting of *Equisetum Telemateia* var. pauciramosum, and *Equisetum Telemateia* forma multirammosum. The second herb of the family Julianiaceae, genus *Amphipterygium adstringens* is selected from the group consisting of cuachalalate.

The method of manufacturing an anti-hemorrhoidal composition includes the steps of admixing an effective amount of a first herb of the genus Equisetaceae and an effective amount of a second herb of the family Julianiaceae, genus *Amphipterygium adstringens* with a solvent to obtain a herbal mixture. The herbal mixture is heated for an effective time period to obtain a prepared herbal mixture. Preferably, the solvent is water. Optionally, the method includes the step of steeping the prepared herbal mixture to obtain a steeped herbal mixture and sifting the steeped herbal mixture to obtain a substantially purified herbal tea. Optionally, the anti-hemorrhoidal composition is packaged. Packaging includes a tea bag, a capsule, a tablet, a concentrated liquid, and a powdered mixture. Preferably, the first herb and the second herb are separately pulverized in a blender and then mixed in a volume ratio of 1 to 1. Similarly, such a pulverization will generally result in a weight ratio of first herb to second herb of one to two. By way of example, the first herb is half as heavy as the second herb.

The method of treating hemorrhoids provided herein includes the step of periodically ingesting a therapeutically effective amount of the composition described above. It is a further object of the present invention to solve the problems articulated in the background section of the invention. The objects and features of the present invention, other than those specifically set forth above, will become apparent in the detailed description of the invention set forth below.

DETAILED DESCRIPTION OF THE INVENTION

Figure 1:
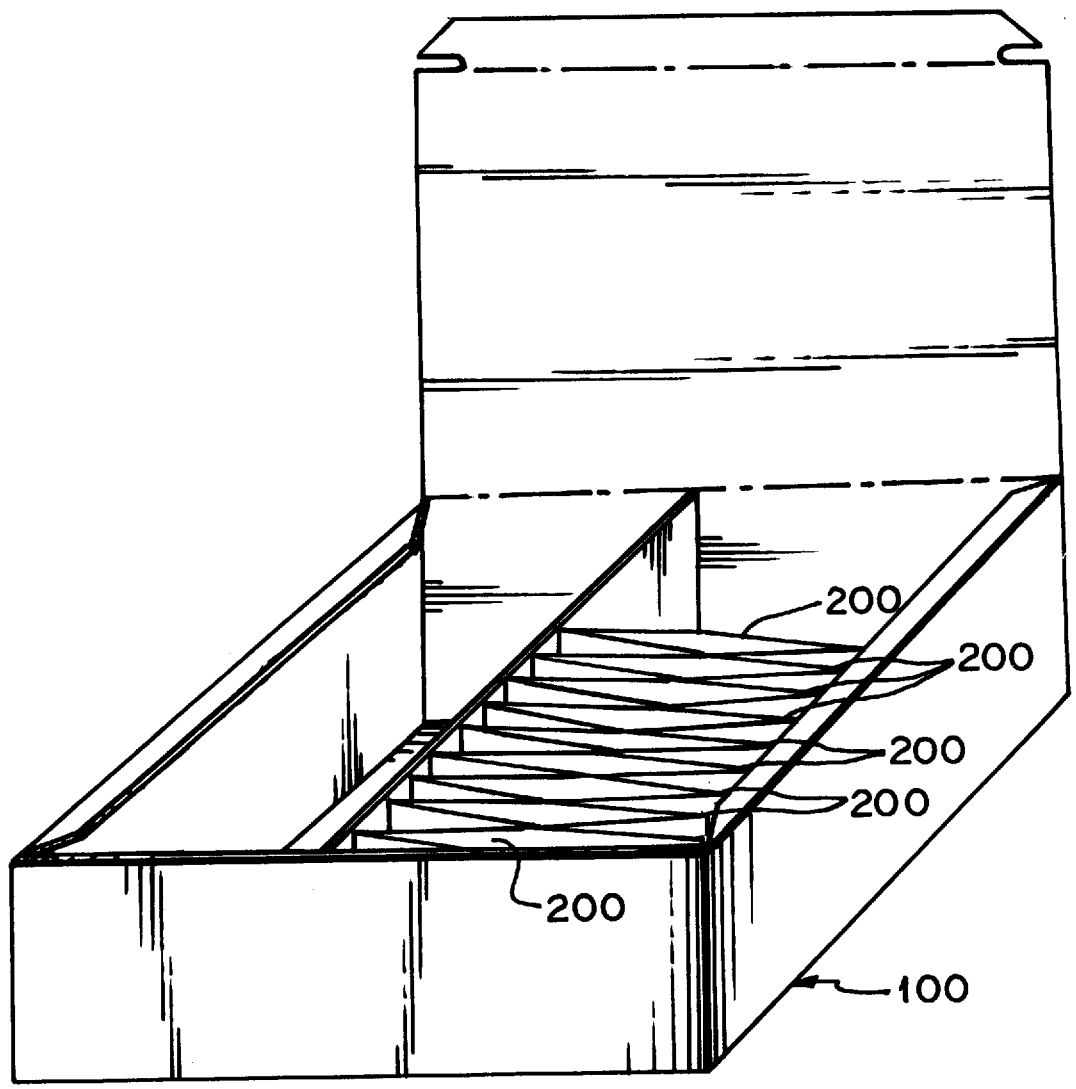
FIG. 1 is a perspective view of the kit of the present invention.

The invention is based upon the discovery that ingestion of a processed composition of matter of a first herb of the genus Equisetaceae and a second herb of the Generie Juliania, family Julianiaceae, genus *Amphipterygium adstringens* (also known as "Cuachalalate") as active ingredients relieves hemorrhoidal symptoms and reduces the swelling of hemorrhoids. Periodic ingestion of a therapeutically effective amount of this composition relieves hemorrhoidal symptoms within a short period of time.

The herb of the genus Equisetaceae is selected from the group consisting of Horsetail (also known as "Canutillo"), *Equisetum arvense* (also known as "Corn Horsetail" and "Field Horsetail"), *Equisetum hyemale* (also known as "Common Scouring Rush"), *Equisetum fluviatile, Equisetum kansanum, Equisetum litorale, Equisetum palustre, Equisetum pratense, Equisetum scirpoides* (also known as "Dwarf Scouring Rush"), *Equisetum sylvaticum* (also known as "Wood Horsetail"), *Equisetum Telemateia, Equisetum variegatum* (also known as "Variegated Rush"), *Equisetum debile, Equisetum elongatum, Equisetum giganteum,* and *Equisetum maximum*.

*Equisetum arvense* (also known as "Great River Horsetail" in one variant) is selected from the group consisting of *Equisetum arvense* var. boreale, *Equisetum arvense* forma alpestre, *Equisetum arvense* forma campestre, *Equisetum arvense* forma diffusum, *Equisetum arvense* forma pseudo-alpestre, *Equisetum arvense* forma pseudo-silvaticum, *Equisetum arvense* forma pseudo-varium, *Equisetum arvense* forma ramulosum, and *Equisetum arvense* forma varium.

*Equisetum hyemale* is selected from the group consisting of *Equisetum hyemale* var. affine (also known as "*Equisetum Prealtum*"), *Equisetum hyemale* var. intermedium, *Equisetum hyemale* var. rubustum, *Equisetum hyemale* forma polystachyum, *Equisetum hyemale* forma proliferum, and *Equisetum hyemale* forma pumilum.

*Equisetum palustre* is selected from the group consisting of *Equisetum palustre* forma arcuatum, *Equisetum palustre* forma filiforme, *Equisetum palustre* forma fluitans, *Equisetum palustre* forma nigridens, *Equisetum palustre* forma polystachion, *Equisetum palustre* forma ramulosum, *Equisetum palustre* forma verticilatum, and *Equisetum palustre* forma simplex.

*Equisetum Telemateia* is selected from the group consisting of *Equisetum Telemateia* var. pauciramosum, and *Equisetum Telemateia* forma multirammosum, *Equisetum Variegatum* is selected from the group consisting of *Equisetum Variegatum* var. jesupi, and *Equisetum Variegatum* var. nelsoni.

The form in which the composition is supplied to the consumer is not critical. It is possible that the composition can be supplied as a homogeneously blended powder of the desired proportion of the requisite herbs. It is further possible that the homogeneously blended powder could be combined with binding agents and formed into water soluble pills and tablets. These pills and tablets can be compressed and shaped.

In accordance with the method of the invention, a therapeutically effective amount of the composition is ingested when symptoms of hemorrhoidal suffering are experienced. Typically, a therapeutically effective quantity is one cup of tea ingested three times a day for a period of one week. One cup daily is then further ingested for approximately another week. Larger quantities of tea are ingested for longer periods of time in cases where the hemorrhoids are severe. The dosage may be adjusted by the user to accommodate differences in body weight and severity of the symptoms. Treatment is continued until relief of hemorrhoidal symptoms and reduction of hemorrhoidal swelling has been achieved.

The present invention further contemplates the addition of unobjectionable adjuvants to the herbal composition such as natural and artificial sweeteners, inert teas, natural flavors, artificial flavors, and coloring agents. Skilled practitioners recognize that addition of the adjuvants affect the weight and volume of the dosage of the herbs at issue. Hence, adjustment of the dosage to account for the presence of the adjuvant is within the skill of the suppliers of the adjuvant products.

FIG. 1 illustrates a perspective view of a kit of the present invention. The kit comprises a container 100 in which a plurality of tea bags 200. Tea bags 200 consist of a permeable membrane or filter commonly made of paper as is known in the art. Preferably, there are in the range of three to over twenty tea bags 200 in container 100 so that a user has a sufficient quantity of tea bags 200 having the compositions described herein for a full, complete treatment of the condition. Preferably, a standardized dosage includes twenty eight (28) tea bags. It is understood that any number of tea bags 200 are used in the kit sufficient to provide a therapeutic effect for a subject. A basic prescription kit includes sufficient tea bags to make 3 cups (3 bags) per day for 7 days (21 units) and sufficient tea bags to make 1 cup (1 bag) per day for 7 days (7 units) for a minimum total of about 28 units. It is understood that the number of tea bags can be in the range of 1 bag to over 200 bags depending on the needs of the subject.

Examples of making the various compositions described herein are provided in the examples provided below. Raw crushed ingredients and/or pulverized ingredients were used herein. Where teaspoons of ingredients were used, the ingredients were generally extremely fine particles that were pulverized. Where tablespoons of ingredients were used, the ingredients were generally crushed and include coarse particles.

EXAMPLE 1

An anti-hemorrhoidal tea was made from the mixture of two herbs: a first herb of the genus Equisetaceae and a second herb of the Generie Juliania, family Julianiaceae, genus *Amphipterygium adstringens*. In particular, about one level tablespoon of crushed cuachalalate herb and one heaping tablespoon of Horsetail herb were added to three cups of cold water in a tea kettle to create a mixture. The mixture was brought to a boil for one minute and allowed to steep for five minutes to form a tea. The tea was then poured into a cup through a sifter, and ingested by a user while still warm. One cup of tea was ingested three times a day for a period of one week. One cup daily was then further ingested for approximately another week. The affliction of hemorrhoids was then cured. Larger quantities of tea are ingested for longer periods of time in cases where the hemorrhoids are severe.

The grounds of the above mixture were also used for a second preparation. The remaining grounds from the preparations discussed above were added to three cups of water. The mixture was allowed to soak overnight. The next morning the mixture was brought to a boil and then ingested as discussed above. A base dosage of the tea was a dosage taken over a period of time of about 14 days in one variant, again depending on the severity of the condition.

EXAMPLE 2

Another example of the anti-hemorrhoidal tea was made from the mixture of two herbs: a first herb of the genus Equisetaceae and a second herb of the Generie Juliania, family Julianiaceae, genus *Amphipterygium adstringens*. Preferably, per cup of solvent, e.g. hot water, about ½ level teaspoon of pulverized horsetail and cuachalalate mixture (or about ¼ teaspoon horsetail and about ¼ teaspoon of cuachalalate) was used. In addition to the ratios of first herb to second herb above, various weight and volume ratios of the respective herbs were used herewith to obtain an effective amount of the combination of the two herbs. Exemplary ratios of the first herb by volume to the second herb include ratios of about one to about ten first herb to about one to about twenty second herb. Larger quantities of tea were ingested for longer periods of time in cases where the hemorrhoids were severe.

EXAMPLE 3

A fifty year old male subject diagnosed with hemmorhoids that included pain and bleeding unsuccessfully utilized numerous hemmorhoid remedies including sitz baths, suppositories, and ligation. The male subject utilized the invention described above under the protocol described above for a period of three weeks. The hemmorhoids were successfully treated.

EXAMPLE 4

Male subject suffering from hemmorhoids for the last twenty-five years. During acute hemmorhoid flare up, subject injested two cups per day of the tea described above for a period of ten days. The hemmorhoids were successfully treated.

EXAMPLE 5

Forty year old male subject suffering from hemmorhoids for two weeks injested three cups per day of the tea described above for a period of two days. The hemmorhoids were successfully treated, and the hemmorhoidal symptoms disappeared.

EXAMPLE 6

Forty-four year old male subject suffering from hemmorhoids for approximately one month injested two cups per day of the tea described above for a period of three days in conjunction with topical application of Anusol® cream. The hemmorhoidal symptoms disappeared.

The present invention also includes a liquified, ready-to-serve composition for the alleviation of hemorrhoidal symptoms such as an iced tea (one made from a powdered constituent(s)) and the like. In this variant a variety of additives are added to the first herb of the genus Equisetaceae and the second herb of the Generie Juliania, family Julianiaceae, genus *Amphipterygium adstringens*.

By way of example, acidulents are selected from the group consisting of fumaric acid, citric acid, malic acid, and ascorbic acid. Of course, other suitable acidulents can also be used herein. Ascorbic acid is a desired constituent of the composition both for its vitamin activity and also since it acts as an oxygen scavenger.

Alginates are also added thereto. Alginates can include propylene glycol (0.1 to 0.2%) to suspend fruit pulp in a fluid of the herbs for added taste. Further carrageenan is also used in the present invention to improve the mouth feel of the herbal preparation. Furcellaran is also used at about (0.05%) to stabilize fruit pulp in the beverage where needed. Gum arabic is also used to optionally stabilize the preparation.

Optionally, the composition comprises a constituent selected from the group consisting of vitamins and minerals. Exemplary vitamins contained therein include vitamin A, vitamin B complex (and the constituents thereof), vitamin C, vitamin D, riboflavin, lactoflavin, flavin, nicotine acid, Betulin compound, ascorbic acid, thiamin, thiamine hydrochloride, thiamine chloride, betataxin, betulin, niacinamide, niacin, calcium, pantothenate, pantothenic acid, nicotinamide, pyridoxine, and tocopherol. Exemplary minerals include calcium, phosphorus, and magnesium, iron, iodine, zinc, and copper. Fiber including cellulose and other non-digestable cell-wall polymers of plant origin can also be added as needed.

The ready to serve variant of the composition further includes an optional color additive. Color additives are natural color additives or artificial color additives. Color additives are selected from the group consisting of Yellow No. 5, Yellow No. 6, Red Nos. 2–4, Blue Nos. 1–2, Violet No. 1, Green No. 3, and Orange B. The color additives described herein are simply examples of the various color additives used in the present invention. By way of example, the FD & C dyes are also used herein. Exemplary uses of color additives herein include adding effective amounts of color additives to the herbal preparation to obtain the following concentrations of color additive in the preparation in parts per million (ppm):

♦ flavor-orange: FD&C yellow #6—in the range of 50–75 ppm; and, FD&C Red #40 of about 5–10 ppm.
♦ flavor-cherry: FD&C red #40—in the range of 50–75 ppm; and, FD&C Blue #1 of about 100 ppm.
♦ flavor-strawberry: FD&C red #40—in the range of 50–60 ppm.
♦ flavor-lemon: FD&C yellow #5—in the range of 10–20 ppm.
♦ flavor-cola or root beer: caramel color in the range of 200–600 ppm.

The resultant color additive should impart maximum color to the herbal preparation, and dissolve without showing the individual component colors. To obtain maximum color, dissolved color is added in solution followed by a moisture removing operation. The showing of individual component colors is minimized with the use or wet-dry blends.

The herbal preparation optionally comprises a natural flavor. Natural flavors include essential oils, protein hydrolysate, distillates, or any products of roasting, heating, or enzymolysis which retains flavoring constituents derived from a spice, vegetable, edible yeast, herb, bark, bud, root, leaf, fruit or fruit juice concentrate, or similar plant material.

The herbal preparation is optionally substantially tableted, capsulated, liquified, and or powdered. Tableting includes exerting a high pressure on the herbal preparation to obtain a suitable size and particle distribution. The herbal preparation is first granulated. Granulation is accomplished by a number of suitable methods by slugging and adding a granulating liquid while mixing the herbal preparation. With slugging, the herbal preparation is run through a tablet press producing a compressed tablet. This tablet is then ground and screened to produce a granulation. An aqueous binder is then added thereto in a mixer. After agglomeration, the resulting material is then dried, ground and appropriately screened.

Optionally, EDTA is added as a preservative. Where constituents are referred to as comprising the herbal preparation it is possible that the powdered mixture consists essentially of, or only consists of these constituents.

While both volume and weight ratios may be used in the practice of the invention, and both provide adequate results, volumes ratios are prefered.

While only a few, preferred embodiments of the invention have been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

I claim:

1. A composition consisting essentially of a first herb of the genus Equisetaceae and a second herb of the genus *Amphipterygium adstringens*.

2. The composition of claim 1 in solid form.

3. A composition consisting essentially of a first herb of the genus Equisetacease, a second herb of the genus *Amphipterygium adstringens*, and a solvent.

4. The composition of claim 3 in which the solvent is water.

5. The composition of claim 1 in which said herb of the genus Equisetaceae is selected from the group consisting of Horsetail, *Equisetum arvense, Equisetum hyemale, Equisetum fluviatile, Equisetum kansanum, Equisetum litorale, Equisetum palustre, Equisetum pratense, Equisetum scirpoides, Equisetum sylvaticum, Equisetum Telemateia, Equisetum variegatum, Equisetum debile, Equisetum elongatum, Equisetum giganteum* and *Equisetum maximum*.

6. The composition of claim 5 in which said *Equisetum arvense* is selected from the group consisting of *Equisetum arvense* var. boreale, *Equisetum arvense* forma alpestre, *Equisetum arvense* forma campestre, *Equisetum arvense* forma diffusum, *Equisetum arvense* forma pseudo-alpestre, *Equisetum arvense* forma pseudo-sylvaticum, *Equisetum arvense* forma pseudo-varium, *Equisetum arvense* forma ramulosum, and *Equisetum arvense* forma varium.

7. The composition of claim 5 in which said *Equisetum hyemale* is selected from the group consisting of *Equisetum hyemale* var. affine, *Equisetum hyemale* var. intermedium, *Equisetum hyemale* var. rubustum, *Equisetum hyemale* forma polystachyum, *Equisetum hyemale* forma proliferum, and *Equisetum hyemale* forma pumilum.

8. The composition of claim 5 in which said *Equisetum palustre* is selected from the group consisting of *Equisetum palustre* forma arcuatum, *Equisetum palustre* forma filiforme, *Equisetum palustre* forma fluitans, *Equisetum palustre* forma nigridens, *Equisetum palustre* forma polystachion, *Equisetum palustre* forma ramulosum, *Equisetum palustre* forma simplex and *Equisetum palustre* forma verticilatum.

9. The composition of claim 5 in which said *Equisetum Telemateia* is selected from the group consisting of *Equisetum Telemateia* var. pauciramosum and *Eguisetum Telemateia* forma multirammosum.

10. The composition of claim 5 in which said *Equisetum variegatum* is selected from the group consisting of *Equisetum variegatum* var. jesupi and *Eguisetum variegatum* var. nelsoni.

11. The composition of claim 1 in which said second herb is cuachalalate.

12. The composition of claim 5 in which said second herb is cuachalalate.

13. The composition of claim 6 in which said second herb is cuachalalate.

14. The composition of claim 7 in which said second herb is cuachalalate.

15. The composition of claim 8 in which said second herb is cuachalalate.

16. The composition of claim 9 in which said second herb is cuachalalate.

17. The composition of claim 10 in which said second herb is cuachalalate.

18. The composition of claim 1 in which the volume of the first herb of the genus Equisetaceae has a volume ratio of about 1:1 with the volume of the second herb of the genus *Amphipterygium adstringens*.

19. The composition of claim 1 in which the weight of the first herb of the genus Equisetaceae has a weight ratio of about 1:2 with the weight of the second herb of the genus *Amphipterygium adstringens*.

20. The composition of claim 2 in which said solid form is selected from the group consisting of powder, capsules and tablets.

21. The composition of claim 20 in which said solid form is powder in a liquid permeable container.

22. The composition of claim 21 in which said liquid is water.

23. A method of relieving hemorrhoidal symptoms which comprises ingesting a therapeutically effective quantity of a composition consisting essentially of a first herb of the genus Equisetacease, a second herb of the genus *Amphipterygium adstringens*, and a solvent.

24. The method of claim 23 in which the solvent is water.

* * * * *

UNITED STATES PATENT AND TRADEMARK OFFICE
CERTIFICATE OF CORRECTION

PATENT NO. : 5,869,059
DATED : February 9, 1999
INVENTOR(S) : Mercedes Flores Garza It is certified that error appears in the above-indentified patent and that said Letters Patent is hereby corrected as shown below:

Title page, item [73], Assignee: change "Mon's" to Mom's--.

Signed and Sealed this

Sixteenth Day of November, 1999

Attest:

Q. TODD DICKINSON

*Attesting Officer*    *Acting Commissioner of Patents and Trademarks*